United States Patent
Honda et al.

(10) Patent No.: US 10,806,680 B2
(45) Date of Patent: *Oct. 20, 2020

(54) DENTAL POLYMERIZABLE COMPOSITION

(71) Applicant: GC Corporation, Shizuoka (JP)

(72) Inventors: Kosuke Honda, Tokyo (JP); Hirosato Kato, Tokyo (JP); Ryosuke Yoshimitsu, Tokyo (JP); Satomi Tateiwa, Tokyo (JP); Toshihiko Tachibana, Tokyo (JP)

(73) Assignee: GC Corporation, Shizuoka (JP)

( * ) Notice: Subject to any disclaimer, the term of this patent is extended or adjusted under 35 U.S.C. 154(b) by 17 days.

This patent is subject to a terminal disclaimer.

(21) Appl. No.: 16/306,968

(22) PCT Filed: Apr. 26, 2017

(86) PCT No.: PCT/JP2017/016611
§ 371 (c)(1),
(2) Date: Dec. 4, 2018

(87) PCT Pub. No.: WO2017/217122
PCT Pub. Date: Dec. 21, 2017

(65) Prior Publication Data
US 2019/0142702 A1    May 16, 2019

(30) Foreign Application Priority Data

Jun. 13, 2016  (JP) ................ 2016-117348

(51) Int. Cl.
| | |
|---|---|
| *A61K 6/30* | (2020.01) |
| *C03C 4/00* | (2006.01) |
| *C03C 12/00* | (2006.01) |
| *C03C 8/06* | (2006.01) |
| *A61K 6/836* | (2020.01) |
| *A61K 6/00* | (2020.01) |
| *A61K 6/831* | (2020.01) |
| *A61K 6/887* | (2020.01) |
| *A61K 6/889* | (2020.01) |
| *C03C 8/04* | (2006.01) |

(52) U.S. Cl.
CPC ........... *A61K 6/836* (2020.01); *A61K 6/00* (2013.01); *A61K 6/831* (2020.01); *A61K 6/887* (2020.01); *A61K 6/889* (2020.01); *C03C 4/0021* (2013.01); *C03C 8/04* (2013.01); *C03C 8/06* (2013.01); *C03C 12/00* (2013.01)

(58) Field of Classification Search
CPC .......... A61K 6/30; A61K 6/831; A61K 6/889; C03C 3/062; C03C 3/078; C03C 3/095; C03C 3/097; C03C 3/112; C03C 12/00; C03C 8/04; C03C 8/06; C03C 4/0021; C03C 4/0007
See application file for complete search history.

(56) References Cited

U.S. PATENT DOCUMENTS

| | | | | |
|---|---|---|---|---|
| 4,209,434 A | * | 6/1980 | Wilson ............... | C08K 3/40 524/443 |
| 4,772,325 A | * | 9/1988 | Kwan ............... | A61K 6/891 106/35 |
| 4,775,592 A | | 10/1988 | Akahane et al. | |
| 4,900,697 A | | 2/1990 | Akahane et al. | |
| 5,032,445 A | * | 7/1991 | Scantlebury ...... | A61C 5/40 428/158 |
| 5,063,257 A | * | 11/1991 | Akahane ........... | A61K 6/889 523/116 |
| 5,618,763 A | | 4/1997 | Frank et al. | |
| 6,217,644 B1 | | 4/2001 | Matsunae et al. | |
| 6,353,039 B1 | | 3/2002 | Rheinberger et al. | |
| 2002/0035025 A1 | | 3/2002 | Schweiger et al. | |
| 2007/0129459 A1 | | 6/2007 | Zeng et al. | |
| 2009/0131551 A1 | * | 5/2009 | Xie .................. | A61K 6/889 523/115 |
| 2009/0208428 A1 | | 8/2009 | Hill et al. | |
| 2010/0311864 A1 | | 12/2010 | Arita et al. | |
| 2011/0009511 A1 | | 1/2011 | Hill et al. | |
| 2014/0056954 A1 | | 2/2014 | O'Donnell et al. | |
| 2017/0105906 A1 | * | 4/2017 | Welch ............... | A61K 6/873 |
| 2017/0296312 A1 | * | 10/2017 | Welch ............... | A61K 6/20 |
| 2019/0083364 A1 | * | 3/2019 | Yoshimitsu ....... | C03C 3/062 |
| 2019/0099332 A1 | * | 4/2019 | Yoshimitsu ....... | A61K 6/831 |
| 2019/0142702 A1 | * | 5/2019 | Honda ............... | A61K 6/00 252/182.12 |

FOREIGN PATENT DOCUMENTS

| | | |
|---|---|---|
| JP | S62-067008 | 3/1987 |
| JP | S63-201038 | 8/1988 |
| JP | H11-268929 | 10/1999 |
| JP | 2000-026225 | 1/2000 |
| JP | 2000-086421 | 3/2000 |
| JP | 2001-130926 | 5/2001 |
| JP | 2002-053339 | 2/2002 |
| JP | 2009-539755 | 11/2009 |
| JP | 2010-532338 | 10/2010 |
| JP | 2010-280630 | 12/2010 |
| JP | 2012-531377 | 12/2012 |
| WO | 90/015782 | 12/1990 |
| WO | 2005/074862 | 8/2005 |
| WO | 2011/000865 | 1/2011 |

OTHER PUBLICATIONS

Smith, D.C., Medical and Dental Applications of Cements, 1971, J. Biomed. Mater. Res. Symposium, John Wiley & Sons, Inc., vol. 1, pp. 189-205, 189-205. (Year: 1971).*
International Search Report for PCT/JP2017/016611 dated Jun. 13, 2017.
International Search Report for PCT/JP2016/085806 dated Jan. 17, 2017.
International Search Report for PCT/JP2016/085805 dated Jan. 17, 2017.
U.S. Office Action for U.S. Appl. No. 16/086,801 dated Jan. 27, 2020.

* cited by examiner

*Primary Examiner* — Elizabeth A. Bolden
(74) *Attorney, Agent, or Firm* — IPUSA, PLLC

(57) ABSTRACT

A dental polymerizable composition including a glass powder and a (meth)acrylate is provided. The glass powder includes zinc, silicon, and fluorine and is substantially free of aluminum.

5 Claims, No Drawings

DENTAL POLYMERIZABLE COMPOSITION

TECHNICAL FIELD

The present invention relates to a dental polymerizable composition.

BACKGROUND ART

In the field of dentistry, dental polymerizable compositions that contain a polymerizable monomer such as a (meth)acrylate and utilize the principle of polymerization to cause setting of the polymerizable monomer are widely used.

Specific examples of dental polymerizable compositions include dental adhesives, dental primers, dental coating materials, dental resin cement, dental composite resins, dental hard resins, dental cutting resin materials, dental temporary restorative materials, and the like.

For example, dental adhesives exhibit their adhesive function by causing polymerization setting of a polymerizable monomer in the presence of a polymerization initiator (see, e.g., Patent Documents 1 to 3).

PRIOR ART DOCUMENTS

Patent Documents

Patent Document 1: Japanese Unexamined Patent Publication No. 2000-26225
Patent Document 2: Japanese Unexamined Patent Publication No. 2000-86421
Patent Document 3: Japanese Unexamined Patent Publication No. 2010-280630

SUMMARY OF THE INVENTION

Problem to be Solved by the Invention

However, a dental polymerizable composition that has improved tooth substance decalcification inhibiting effects is desired.

In this respect, an object of one embodiment of the present invention is to provide a dental polymerizable composition that is capable of effectively inhibiting tooth substance decalcification.

Means for Solving the Problem

According to one embodiment of the present invention, a dental polymerizable composition including a glass powder and a (meth)acrylate is provided. The glass powder includes zinc, silicon, and fluorine and is substantially free of aluminum.

Advantageous Effect of the Invention

According to an aspect of the present invention, a dental polymerizable composition that is capable of effectively inhibiting tooth substance decalcification may be provided.

EMBODIMENTS FOR IMPLEMENTING THE INVENTION

In the following, embodiments for implementing the present invention will be described.

<Dental Polymerizable Composition>

A dental polymerizable composition according to an embodiment of the present invention includes a glass powder and a (meth)acrylate.

Specific forms of the dental polymerizable composition include, for example, dental adhesive, dental primer, dental coating material, dental resin cement, dental composite resin, dental hard resin, dental cutting resin material, dental temporary restorative material, and the like.

Note that the dental polymerizable composition may be either a single-component type dental composition or a two-component type dental composition.

Also, when using the dental polymerizable composition, a tooth surface treating agent (see, e.g., Patent Document 2) may be used as necessary.

<Glass Powder>

The glass powder according to the present embodiment contains zinc, silicon, and fluorine and is substantially free of aluminum. In this way, the tooth substance decalcification inhibiting effect of the dental polymerizable composition may be improved.

Note that in the present description and claim, the expression "substantially free of aluminum" means the aluminum content, in terms of the amount of aluminum oxide ($Al_2O_3$) in the glass powder, is less than or equal to 1 mass %.

The expression is given the above definition in view of the fact that even if an aluminum compound is not included in the raw material composition of the glass powder, an aluminum compound may be mixed into the raw material composition as an impurity in the manufacturing process of the glass powder, or aluminum may be erroneously detected by a fluorescent X-ray analyzer that determines the composition of the glass powder, for example. Normally, unless an aluminum compound is added to the raw material composition of the glass powder, the aluminum content, in terms of the amount of aluminum oxide ($Al_2O_3$) in the glass powder, would not exceed 1 mass %.

The aluminum content, in terms of the amount of aluminum oxide ($Al_2O_3$) in the glass powder, is preferably in the range from 0 to 0.5 mass %, and more preferably in the range from 0 to 0.3 mass %.

The zinc content, in terms of the amount of zinc oxide (ZnO) in the glass powder, is preferably in the range from 10 to 60 mass %, and more preferably in the range from 20 to 55 mass %. When the zinc content, in terms of the amount of zinc oxide (ZnO) in the glass powder, is greater than or equal to 10 mass %, the tooth substance decalcification inhibiting effect of the glass powder may be further improved, and when the zinc content of the glass powder is less than or equal to 60 mass %, a glass powder having high transparency may be easily obtained.

The silicon content, in terms of the amount of silicon oxide ($SiO_2$) in the glass powder, is preferably in the range from 15 to 50 mass %, and more preferably in the range from 20 to 40 mass %. Note that silicon plays a role of forming a network in glass. When the silicon content, in terms of the amount of silicon oxide ($SiO_2$) in the glass powder, is greater than or equal to 15 mass %, a glass powder with high transparency may be easily obtained, and when the silicon content of the glass powder is less than or equal to 50 mass %, a dental polymerizable composition having a desirable curing property may be easily obtained.

The fluorine (F) content of the glass powder is preferably in the range from 1 to 30 mass %, and more preferably in the range from 3 to 20 mass %. When the fluorine (F) content of the glass powder is greater than or equal to 1 mass %, a tooth substance reinforcing effect may be exhibited, and when the fluorine (F) content of the glass powder is less than or equal to 30 mass %, a dental polymerization composition having a desired curing property may be more easily obtained.

The glass powder may further contain calcium, phosphorus, strontium, lanthanum, sodium, potassium, and the like.

The calcium content, in terms of the amount of calcium oxide (CaO) in the glass powder, is preferably in the range from 0 to 30 mass %, and more preferably in the range from 5 to 20 mass %. By including calcium in the glass powder, the operability of the dental polymerizable composition may be improved.

The phosphorus content, in terms of the amount of phosphorus(V) oxide ($P_2O_5$) in the glass powder, is preferably in the range from 0 to 10 mass %, and more preferably in the range from 0 to 5 mass %. By including phosphorus in the glass powder, the operability of the dental polymerizable composition may be improved.

The strontium content, in terms of the amount of strontium oxide (SrO) in the glass powder, is preferably in the range from 0 to 40 mass %, and more preferably in the range from 10 to 30 mass %. By including strontium in the glass powder, the radiopacity of a set product of the dental polymerizable composition may be improved.

The lanthanum content, in terms of the amount of lanthanum oxide ($La_2O_3$) in the glass powder, is preferably in the range from 0 to 50 mass %, and more preferably in the range from 10 to 40 mass %. By including lanthanum in the glass powder, the acid resistance of the set product of the dental polymerizable composition may be improved.

The sodium content, in terms of the amount of sodium oxide ($Na_2O$) in the glass powder, is preferably in the range from 0 to 15 mass %, and more preferably in the range from 1 to 10 mass %. By including sodium in the glass powder, the refractive index of the glass powder may be decreased, and a glass powder with high transparency may be easily obtained.

The potassium content, in terms of the amount of potassium oxide ($K_2O$) in the glass powder, is preferably in the range from 0 to 10 mass %, and more preferably in the range from 1 to 5 mass %. By including potassium in the glass powder, the refractive index of the glass powder may be decreased, and a glass powder with high transparency may be easily obtained.

The number average particle diameter of the glass powder is preferably in the range from 0.02 to 30 µm, and more preferably in the range from 0.02 to 20 µm. When the number average particle diameter of the glass powder is greater than or equal to 0.02 µm, the operability of the dental polymerizable composition may be improved, and when number average particle diameter of the glass powder is less than or equal to 30 µm, the abrasion resistance of the set product of the dental polymerizable composition may be improved.

The content of the glass powder in the dental polymerizable composition is preferably in the range from 5 to 60 mass %, and more preferably in the range from 10 to 50 mass %. When the content of the glass powder in the dental polymerizable composition is greater than or equal to 5 mass %, the tooth substance decalcification inhibiting effect of the dental polymerizable composition may be improved, and when the content of the glass powder in the dental polymerizable composition is less than or equal to 60 mass %, the adhesiveness of the dental polymerizable composition may be improved.

<Method for Producing Glass Powder>

The glass powder according to the present embodiment may be produced by melting a raw material composition that includes a zinc compound, a silicon compound, and a fluorine compound but does not include an aluminum compound, and then pulverizing the raw material composition.

Examples of the zinc compound include, but are not limited to, zinc oxide, zinc fluoride, and a combination of two or more types of zinc compounds.

Examples of the silicon compound include, but are not limited to, anhydrous silicic acid, and a combination of two or more types of silicon compounds.

Examples of the fluorine compound include, but are not limited to, calcium fluoride, strontium fluoride, sodium fluoride, and a combination of two or more types of fluorine compounds.

The raw material composition may further contain a calcium compound, a phosphorus compound, a strontium compound, a lanthanum compound, a sodium compound, a potassium compound, and the like.

Examples of the calcium compound include, but are not limited to, calcium fluoride, calcium phosphate, calcium carbonate, calcium hydroxide, and a combination of two or more types of calcium compounds.

Examples of the phosphorus compound include, but are not limited to, calcium phosphate, strontium phosphate, sodium dihydrogenphosphate, and a combination of two or more types of phosphorus compounds.

Examples of the strontium compound include, but are not limited to, strontium fluoride, strontium hydroxide, strontium carbonate, strontium oxide, strontium phosphate and the like can be mentioned, and a combination of two or more types of strontium compounds.

Examples of the lanthanum compound include, but are not limited to, lanthanum fluoride, lanthanum oxide and the like can be mentioned, and a combination of two or more types of lanthanum compounds.

Examples of the sodium compound include, but are not limited to, sodium dihydrogenphosphate, sodium carbonate, sodium fluoride, and a combination of two or more types of sodium compounds.

Examples of the potassium compound include, but are not limited to, potassium fluoride, potassium carbonate, potassium hydrogencarbonate, dipotassium hydrogen phosphate, and a combination of two or more types of potassium compounds.

Note that the compounds included in the raw material composition may be combined at corresponding ratios based on the composition of the glass powder excluding aluminum.

<(Meth)acrylate>

In the present description and claim, (meth)acrylate refers to various types of monomers, oligomers, and prepolymers of acrylates or methacrylates that include at least one (meth)acryloyloxy group.

Examples of the (meth)acrylate include, but are not limited to, methyl (meth)acrylate, ethyl (meth)acrylate, isopropyl (meth)acrylate, n-butyl (meth)acrylate, isobutyl (meth)acrylate, hydroxypropyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth)acrylate, 2-ethylhexyl (meth)acrylate, benzyl (meth)acrylate, 2-hydroxy-1,3-di(meth)acryloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutylene glycol di(meth)acrylate, bisphenol A diglycidyl (meth)acrylate, di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H, 5H)triazine-2,4,6-trione, 2,2-bis-4-(3-(meth)acryloyloxy-2-hydroxypropyl)-phenylpropane, N,N'-(2,2,4-trimethylhexamethylene) bis[2-(aminocarboxy)propane-1,3-diol]tetramethacrylate, a urethane methacrylate oligomer composed of 2,2'-bis(4-hydroxycyclohexyl)propane, 2-oxypanone, hexamethylene diisocyanate, and 2-hydroxy (meth)acrylate, a urethane methacrylate oligomer composed of 1,3-butanediol, hexamethylene diisocyanate, and 2-hydroxyethyl (meth)acrylate, and a combination of two or more types of (meth)acrylates.

Note that a (meth)acrylate including an acid group may also be used.

The (meth)acrylate including an acid group may include a plurality of acid groups.

By adding a (meth)acrylate including an acid group to the dental polymerizable composition according to the present embodiment, the dental polymerizable composition may exhibit adhesiveness to tooth substance, ceramics such as zirconia and alumina that are used as dental restoration materials, and alloys containing precious metal, for example.

The acid group is preferably a phosphoric acid group or a carboxyl group.

A phosphoric acid group exhibits stronger acidity as compared with a carboxyl group, and as such, using a (meth)acrylate including a phosphoric acid group may bring about the effects of dissolving a smear layer on a tooth surface and decalcifying tooth substance, and may particularly contribute to the effect of improving adhesiveness of the dental polymerizable composition to enamel.

Examples of (meth)acrylates including a phosphoric acid group include 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)acryloyloxydecyl dihydrogen phosphate, 6-(meth)acryloyloxyhexylphenyl hydrogen phosphate, 10-(meth)acryloyloxydecyl dihydrogen phosphate, 1,3-di(meth)acryloylpropane-2-dihydrogen phosphate, 1,3-di(meth)acryloylpropane-2-phenylhydrogen phosphate, bis[5-{2-(meth)acryloyloxyethoxycarbonyl}heptyl]hydrogen phosphate, and the like. From among the above-mentioned (meth)acrylates, 10-(meth)acryloyloxydecyl dihydrogen phosphate is particularly suitable in view its contributing effects to improving adhesiveness of the dental polymerizable composition and stability of the (meth)acrylate itself.

Examples of (meth)acrylates including a carboxyl group include 4-(meth)acryloxyethyltrimellitic acid, 4-(meth)acryloxyethyltrimellitic anhydride, 4-(meth)acryloxydecyltrimellitic acid, 4-(meth)acryloxydecyl trimellitic anhydride, 11-(meth)acryloyloxy-1,1-undecane dicarboxylic acid, 1,4-di(meth)acryloyloxy pyromellitic acid, 2-(meth)acryloyloxy ethyl maleic acid, 2-(meth)acryloyloxyethyl phthalic acid, 2-(meth)acryloyloxyethyl hexahydrophthalic acid, and the like. From among the above-mentioned (meth)acrylates, 4-(meth)acryloxyethyl trimellitic acid and 4-(meth)acryloxyethyl trimellitic anhydride are particularly suitable in view of their contributing effects to improving adhesiveness of the dental polymerizable composition.

The content of the (meth)acrylate in the dental polymerizable composition is preferably in the range from 20 to 90 mass %, and more preferably in the range from 30 to 80 mass %. When the content of the (meth)acrylate in the dental polymerizable composition is greater than or equal to 20 mass %, the adhesiveness of the dental polymerizable composition may be improved, and when the content of the (meth)acrylate in the dental polymerizable composition is less than or equal to 90 mass %, other components can be included in the dental polymerizable composition at desirable amounts and the performance of the dental polymerizable composition may be further improved.

<Polymerization Initiator>

The dental polymerizable composition according to the present embodiment preferably further includes a polymerization initiator.

The method for initiating polymerization of the (meth)acrylate is not particularly limited, and for example, energy necessary for initiating polymerization may be supplied to the dental polymerizable composition according to the present embodiment in the form of heat, visible light, electromagnetic waves (infrared rays, ultraviolet rays, X rays), and the like.

Regardless of the method used for initiating polymerization of the (meth)acrylate, by including a polymerization initiator in the dental polymerizable composition according to the present embodiment, the energy required for initiating polymerization of the (meth)acrylate monomers may be substantially reduced, and control of the polymerization reaction may be facilitated.

Note that a chemical polymerization initiator may be used as the polymerization initiator, for example. In this case, a combination of an oxidizing agent and a reducing agent may be used as the chemical polymerization initiator. For example, in a case where the dental polymerizable composition is made up of one component containing an oxidizing agent and another component containing a reducing agent, by mixing the two components together, polymerization of the (meth)acrylate may be initiated and setting of the dental polymerizable composition may be promoted.

Examples of the oxidizing agent include, but are not limited to, peroxides such as cumene hydroperoxide, diisopropylbenzene hydroperoxide, di-t-butyl peroxide, lauroyl peroxide, benzoyl peroxide, t-butyl peroxy isopropyl carbonate, t-butyl peroxy-2-ethyl hexanoate; azo compounds such as azobisisobutyronitrile, 1,1'-azobis(cyclohexanecarbonitrile), 2,2'-azobis(2,4-dimethylvaleronitrile), dimethyl 2,2'-azobis(2-methyl propionate); hydrogen peroxide; persulfates; and a combination of two or more types of oxidizing agents.

The content of the oxidizing agent in the dental polymerizable composition is preferably in the range from 0.1 to 10 mass %, and more preferably in the range from 0.2 to 5 mass %. When the content of the oxidizing agent in the dental polymerizable composition is greater than or equal to 0.1 mass %, the adhesiveness of the dental polymerizable composition may be improved, and when the content of the oxidizing agent in the dental polymerizable composition is less than or equal to 10 mass %, the storage stability of the dental polymerization composition may be improved.

Examples of the reducing agent include, but are not limited to, tertiary amines such as N,N-dimethyl-p-toluidine, triethanolamine, tolyldiethanolamine, methyl 4-dimethylaminobenzoate, ethyl 4-dimethylaminobenzoate, isoamyl 4-dimethylaminobenzoate; N-phenylglycine; sodium p-toluenesulfinate; sodium benzenesulfinate; and a combination of two or more types of reducing agents.

The content of the reducing agent in the dental polymerizable composition is preferably in the range from 0.1 to 10 mass %, and more preferably in the range from 0.2 to 5 mass %. When the content of the reducing agent in the dental polymerizable composition is greater than or equal to 0.1 mass %, and when the content of the reducing agent in the dental polymerizable composition is less than or equal to 10 mass %, the adhesiveness of the dental polymerizable composition may be further improved.

Also, note that a photopolymerization initiator may be used in place of the chemical polymerization initiator or together with the chemical polymerization initiator, for example. When the dental polymerizable composition includes a photopolymerization initiator, polymerization of the (meth)acrylate may be initiated and setting of the dental polymerizable composition may be promoted by irradiating light onto the dental polymerizable composition.

Examples of the photopolymerization initiator include, but are not limited to, a ketone-based compound, an α-diketone-based compound, a ketal-based compound, an anthraquinone-based compound, a thioxanthone-based compound, a benzoin alkyl ether-based compound, an acylphosphine oxide-based compound, and a combination of two or more types of photopolymerization initiators.

Examples of the ketone-based compound include benzophenone, bis(4-dimethylaminophenyl)ketone, 4,4'-bis(diethylamino)benzophenone, and the like.

Examples of the α-diketone-based compound include camphorquinone, benzyl, diacetyl, acenaphthenequinone, 9,10-phenanthraquinone, and the like.

Examples of the ketal-based compound include benzyl ketal, diacetyl ketal, benzyl dimethyl ketal, benzyl diethyl ketal, benzyl bis(β-phenylethyl)ketal, benzyl bis(2-methoxyethyl)ketal, 4,4'-dimethyl(benzyl dimethyl ketal), and the like.

Examples of the anthraquinone-based compound include anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, and the like.

Examples of the thioxanthone-based compound include thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, 2-ethylthioxanthone, 2-chlorothioxanthone, 2-hydroxy-3-(3,4-dimethyl-9-oxo-9H-thioxanthen-2-yloxy)-N,N,N-trimethyl-1-propanaminium chloride, and the like.

Examples of the benzoin alkyl ether-based compound include benzoin methyl ether, benzoin ethyl ether, benzoin propyl ether, benzoin isobutyl ether, and the like.

Examples of the acylphosphine oxide-based compound include 2,4,6-trimethylbenzoyldiphenylphosphine oxide, 2,4,6-trimethoxybenzoyldiphenylphosphine oxide, 2,6-dimethylbenzoyldiphenylphosphine oxide, 2,6-dimethoxybenzoyldiphenylphosphine oxide, and the like.

The content of the photopolymerization initiator in the dental polymerizable composition is preferably in the range from 0.1 to 10 mass %, and more preferably in the range from 0.2 to 5 mass %. When the content of the photopolymerization initiator in the dental polymerizable composition is greater than or equal to 0.1 mass %, the adhesiveness of the dental polymerizable composition may be improved, and when the content of the photopolymerization initiator in the dental polymerizable composition is less than or equal to 10 mass %, the storage stability of the dental polymerizable composition may be improved.

Note that when using a photopolymerization initiator as the polymerization initiator, a photopolymerization accelerator may be used in combination, for example.

Examples of the photopolymerization accelerator include, but are not limited to, tertiary amines such as N,N-dimethyl-p-toluidine, triethanolamine, tolyldiethanolamine, methyl 4-dimethylaminobenzoate, ethyl 4-dimethylaminobenzoate, isoamyl 4-dimethylaminobenzoate; barbituric acid derivatives such as barbituric acid, 1,3-dimethylbarbituric acid, 1,3,5-trimethylbarbituric acid, 1,3,5-triethylbarbituric acid, 5-butylbarbituric acid, 1-benzyl-5-phenylbarbituric acid, and 1-cyclohexyl-5-ethylbarbituric acid; and a combination of two or more types of photopolymerization accelerators.

The content of the photopolymerization accelerator in the dental polymerizable composition is preferably in the range from 0.1 to 5 mass %, and more preferably in the range from 0.2 to 1 mass %. When the content of the photopolymerization accelerator in the dental polymerizable composition is greater than or equal to 0.1 mass % and less than or equal to 5 mass %, the adhesiveness of the dental polymerizable composition may be further improved.

<Other Ingredients>

The dental polymerizable composition may further include a polymerization inhibitor and a filler other than the glass powder according to the present embodiment.

Examples of the polymerization inhibitor include, but are not limited to, dibutylhydroxytoluene, 2,6-t-butyl-2,4-xylenol, and a combination of two or more types of polymerization inhibitors.

The content of the polymerization inhibitor in the dental polymerizable composition is preferably in the range from 0.1 to 5 mass %, and more preferably in the range from 0.2 to 1 mass %. When the content of the polymerization inhibitor in the dental polymerizable composition is greater than or equal to 0.1 mass % and less than or equal to 5 mass %, the storage stability of the dental polymerizable composition may be improved.

The filler other than the glass powder according to the present embodiment may be either an organic filler or an inorganic filler but is preferably an inorganic filler.

Examples of the inorganic filler include, but is not limited to, silica powder, glass powder other than the glass powder according to the present embodiment (e.g., barium glass powder, fluoroaluminosilicate glass powder, and the like), and a combination of two or more types of inorganic fillers.

Note that the inorganic filler may be treated with a surface treating agent such as a silane coupling agent as necessary.

The content of the filler other than the glass powder according to the present embodiment in the dental polymerizable composition is preferably in the range from 0.1 to 20 mass %, and more preferably in the range from 0.5 to 10 mass %. When the content of the filler other than the glass powder according to the present embodiment in the dental polymerizable composition is greater than or equal to 0.1 mass % and less than or equal to 20 mass %, the adhesiveness of the dental polymerizable composition may be further improved.

EXAMPLES

In the following, the present invention will be described in further detail with reference to examples and comparative examples. Note, however, that the present invention is not limited to these examples.

Examples 1 to 14

[Production of Glass Powder]

In each example, zinc oxide (ZnO), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogencarbonate ($KHCO_3$) were combined at a predetermined ratio and were sufficiently mixed and agitated using a mortar. The obtained mixture was then placed in a platinum crucible and placed in an electric furnace. The electric furnace was heated to 1300° C. to cause the mixture to melt and be sufficiently homogenized, and thereafter, the mixture was poured into water to form a lump of glass. The obtained lump of glass was subjected to dry pulverization for 20 hours using a ball mill made of alumina and then passed through a 120 mesh sieve. Further, wet pulverization was carried out for 66 hours using a ball mill made of alumina to obtain a glass powder.

Then, the number average particle diameter and composition of the glass powder were evaluated.

<Particle Diameter of Glass Powder>

The particle size distribution of the glass powder was measured using a laser diffraction particle size analyzer LA-950 (manufactured by Horiba Ltd.).

Tables 1 and 2 indicate the number average particle diameter of the glass powder obtained by the above measurement.

<Composition of Glass Powder>

The glass powder was analyzed using a fluorescent X-ray analyzer ZSX Primus II (manufactured by Rigaku Corporation) to determine its composition.

Table 1 indicates the composition of the glass powder (mass %) determined by the above analysis.

Note that the contents of Zn, Al, Si, Ca, P, Sr, La, Na and K are respectively expressed in terms of the amounts of ZnO, $Al_2O_3$, $SiO_2$, CaO, $P_2O_5$, SrO, $La_2O_3$, $Na_2O$, and $K_2O$ in the glass powder.

Note that although no aluminum compound was added to the raw material compositions of Examples 1 to 13, 0.1 to 0.5 mass % of aluminum in terms of the amount of aluminum oxide ($Al_2O_3$) was detected in the glass powders. The presence of aluminum in the glass powder may be attributed to alumina derived from an alumina ball or an alumina pot used at the time of pulverization being mixed into the glass powder or a detection error of the fluorescent X-ray analyzer, for example.

[Production of Adhesive]

In each example, an adhesive was prepared by mixing the glass powder, a methacrylate, a polymerization initiator, a polymerization accelerator, a polymerization inhibitor, and a filler at the ratio [mass %] indicated in Tables 1A and 1B.

Note that the adhesive of Example 7 was a two-component type adhesive and was prepared by mixing together a first component and a second component at a ratio of 1:1 (mass %). The adhesives of the examples other than Example 7 were single-component type adhesives.

Note that the abbreviations in Tables 1A and 1B stand for the following substances.

(Methacrylate)
HEMA: 2-hydroxyethyl methacrylate
NPG: neopentyl glycol dimethacrylate
3G: triethylene glycol dimethacrylate (manufactured by Shin-Nakamura Chemical Co., Ltd.)
Bis-GMA: bisphenol A glycidyl methacrylate (2,2-bis[4-(2-hydroxy-3-methacryloyloxypropoxy)phenyl]propane)
UDMA: di-2-methacryloyloxyethyl-2,2,4-trimethylhexamethylene dicarbamate
MDP: 10-methacryloyloxydecyl dihydrogen phosphate
(Photopolymerization Initiator)
CQ: camphorquinone
TPO: 2,4,6-trimethoxybenzoyl diphenylphosphine oxide (manufactured by BASF)
(Photopolymerization Accelerator)
EPA: ethyl 4-dimethylaminobenzoate
(Oxidizing Agent in Chemical Initiator)
BPO: benzoyl peroxide
(Reducing Agent in Chemical Initiator)
PA: p-tolyldiethanolamine
(Polymerization Inhibitor)
BHT: Dibutylhydroxytoluene (Filler)
Inorganic filler: Aerosil R972 having a number average particle diameter of 0.2 μm (manufactured by Nippon Aerosil Co., Ltd.)

Comparative Examples 1 to 7

[Production of Glass Powder]

In each comparative example, zinc oxide (ZnO), aluminum oxide ($Al_2O_3$), aluminum fluoride ($AlF_3$), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogencarbonate ($KHCO_3$) were combined at a predetermined ratio and were sufficiently mixed and agitated using a mortar. The obtained mixture was then placed in a platinum crucible and placed in an electric furnace. The electric furnace was heated to 1300° C. to cause the mixture to melt and be sufficiently homogenized, and thereafter, the mixture was poured into water to form a lump of glass. The obtained lump of glass was subjected to dry pulverization for 20 hours using a ball mill made of alumina and then passed through a 120 mesh sieve. Further, wet pulverization was carried out for 66 hours using a ball mill made of alumina to obtain a glass powder.

[Production of Adhesive]

In each comparative example, an adhesive was prepared by mixing the glass powder, methacrylate, a polymerization initiator, a polymerization accelerator, a polymerization inhibitor, and a filler at the ratio [mass %] indicated in Table 2.

Note that the adhesives of Comparative Examples 1 to 7 were single-component type adhesives.

Then, the tooth substance decalcification inhibiting effect and adhesiveness of the adhesives were evaluated.

<Tooth Substance Decalcification Inhibiting Effect>

A bonding material, G-Premio Bond (manufactured by GC Corporation), was applied to bovine dentin, after which the bovine dentin was left as is for 10 seconds and then dried with high pressure air for 5 seconds. Then, after applying an adhesive, weak pressure air was used to thinly spread the adhesive. Further, light was irradiated in Mode 20 using a light irradiator, G-Light Prima (manufactured by GC Corporation), to cause setting of the bonding material and the adhesive.

Then, the bovine dentin having set products of the bonding material and the adhesive formed thereon was immersed in a decalcification liquid (50 mM acetic acid, 1.5 mM calcium chloride, 0.9 mM potassium dihydrogen phosphate, pH 4.5) at 37° C. for 24 hours.

Then, an image of the bovine dentin having set products of the bonding material and the adhesive formed thereon was captured through x-ray transmission using an X-ray inspection apparatus (CT), and the captured image was analyzed using image processing software to determine the amount of mineral loss and evaluate the tooth substance decalcification inhibiting effect. The categories of the rating scale used for evaluating the tooth substance decalcification inhibiting effect are as follows.

A: amount of mineral loss is less than 3100 volume %·μm
B: amount of mineral loss is greater than or equal to 3100 volume %·μm and less than 3600 volume %·μm
C: amount of mineral loss is greater than or equal to 3600 volume %·μm Note that bovine dentin that was not coated with a bonding material and an adhesive was subjected to the tooth substance decalcification inhibiting effect evaluation in the same manner as described above except that the bonding material and the adhesive were not applied. As a result, the amount of mineral loss was greater than or equal to 4557 volume %·μm.

[Adhesiveness]

A crown portion of a bovine lower jaw anterior tooth was embedded in a room temperature polymerizing resin with the labial surface exposed, and then polished using SiC abrasive paper having a particle size of 320 until enamel (or dentin) was exposed.

The bonding material, G-Premio Bond (manufactured by GC Corporation), was applied to the polished dentin, left as is for 10 seconds, and then dried with high pressure air for 5 seconds. Then, after applying an adhesive, weak pressure air was used to thinly spread the adhesive. Further, a mold (manufactured by ULTRADENT Co., Ltd.) having a hole with a diameter of 2.38 mm was placed on the surface of the dentin coated with the adhesive to define the area of an adherend, and thereafter, light was irradiated in Mode 10 using the light irradiator, G-Light Prima (manufactured by GC Corporation), to cause setting of the bonding material and the adhesive. Then, after filling the mold with Clearfill AP-X (manufactured by Kuraray Co., Ltd.) as a composite resin, light was irradiated in Mode 20 using the light irradiator, G-Light Prima (manufactured by GC Corporation), to cause setting of the composite resin. Further, the dentin was kept in water at 37° C. for 24 hours to obtain a test sample.

Shear tests were carried out on 5 test samples using a compact table-top testing machine, EZ-S (manufactured by Shimadzu Corporation), at a crosshead speed of 1 mm/min, an average value of the adhesive strength of the adhesive with respect to enamel (or dentin) was obtained, and the adhesiveness of the adhesive was evaluated based thereon. The categories of the rating scale used to evaluate the adhesiveness are as follows.

A: average value of the adhesive strength is greater than or equal to 25 MPa
B: average value of the adhesive strength is less than 25 MPa The evaluations of the tooth substance decalcification inhibiting effect and the adhesiveness of the adhesives obtained in the examples and comparative examples are indicated in Table 1A, Table 1B, and Table 2.

TABLE 1A

| | EXAMPLE | | | | | | |
|---|---|---|---|---|---|---|---|
| | 1 | 2 | 3 | 4 | 5 | 6 | 7 |
| GLASS POWDER | | | | | | | |
| Zn | 50.5 | 50.5 | 50.5 | 50.5 | 50.5 | 50.5 | 50.5 |
| F | 3.0 | 3.0 | 3.0 | 3.0 | 3.0 | 3.0 | 3.0 |
| Al | 0.3 | 0.3 | 0.3 | 0.3 | 0.3 | 0.3 | 0.3 |
| Si | 33.0 | 33.0 | 33.0 | 33.0 | 33.0 | 33.0 | 33.0 |
| Ca | 13.2 | 13.2 | 13.2 | 13.2 | 13.2 | 13.2 | 13.2 |
| P | | | | | | | |
| Sr | | | | | | | |
| La | | | | | | | |
| Na | | | | | | | |
| K | | | | | | | |
| TOTAL | 100 | 100 | 100 | 100 | 100 | 100 | 100 |
| NUMBER AVERAGE PARTICLE DIAMETER [μm] | 0.5 | 0.5 | 0.5 | 0.5 | 0.5 | 0.5 | 0.5 |
| ADHESIVE | | | | | | | |
| GLASS POWDER | 10 | 20 | 40 | 20 | 20 | 20 | 20  20 |
| HEMA | 19 | 18 | 13.5 | 18 | 18 | 18 | 19  19 |
| NPG | 19 | 18 | 13.5 | | 18 | 18 | 19  19 |

TABLE 1A-continued

| | EXAMPLE | | | | | | |
|---|---|---|---|---|---|---|---|
| | 1 | 2 | 3 | 4 | 5 | 6 | 7 |
| 3G | | | | 18 | 18 | | |
| Bis-GMA | 38 | 35 | 27 | 35 | | 25 | 37.5  37.5 |
| UDMA | | | | | 35 | | |
| MDP | | | | | | 10 | |
| CQ | 2 | 1.8 | 1.5 | 1.8 | 1.8 | 1.8 | |
| TPO | 1.5 | 1.2 | 1.1 | 1.2 | 1.2 | 1.2 | |
| EPA | 4 | 3.5 | 3 | 3.5 | 3.5 | 3.5 | |
| BPO | | | | | | | 2 |
| PA | | | | | | | 2 |
| BHT | 0.5 | 0.5 | 0.4 | 0.5 | 0.5 | 0.5 | 0.5  0.5 |
| INORGANIC FILLER | 6 | 2 | | 2 | 2 | 2 | 2  2 |
| TOTAL | 100 | 100 | 100 | 100 | 100 | 100 | 100  100 |
| TOOTH SUBSTANCE DECALCIFICATION INHIBITING EFFECT | | | | | | | |
| MINERAL LOSS [VOLUME %-μm] | 2498 | 2388 | 2267 | 2511 | 2468 | 2403 | 2368 |
| EVALUATION | A | A | A | A | A | A | A |
| ADHESIVENESS | | | | | | | |
| ENAMEL | A | A | A | A | A | A | A |
| DENTIN | A | A | A | A | A | A | A |

TABLE 1B

| | EXAMPLE | | | | | | |
|---|---|---|---|---|---|---|---|
| | 8 | 9 | 10 | 11 | 12 | 13 | 14 |
| GLASS POWDER | | | | | | | |
| Zn | 30.0 | 26.4 | 23.8 | 45.0 | 49.5 | 41.7 | 25.2 |
| F | 5.2 | 6.5 | 6.8 | 3.3 | 3.2 | 4.7 | 5.8 |
| Al | 0.3 | 0.3 | 0.5 | 0.3 | 0.1 | 0.3 | 0.2 |
| Si | 22.9 | 24.7 | 23.1 | 35.5 | 34.8 | 37.7 | 26.8 |
| Ca | 7.1 | 9.6 | 9.3 | 11.4 | | 12.1 | 6.6 |
| P | | | | | 4.5 | | |
| Sr | | | | | 12.4 | | |
| La | 34.5 | 32.5 | 36.5 | | | | 33.2 |
| Na | | | | | | 3.5 | |
| K | 2.2 | | | | | | |
| TOTAL | 100 | 100 | 100 | 100 | 100 | 100 | 100 |
| NUMBER AVERAGE PARTICLE DIAMETER [μm] | 0.7 | 0.7 | 0.7 | 0.6 | 0.6 | 0.4 | 0.5 |
| ADHESIVE | | | | | | | |
| GLASS POWDER | 20 | 20 | 20 | 20 | 20 | 20 | 20 |
| HEMA | 18 | 18 | 18 | 18 | 18 | 18 | 18 |
| NPG | 18 | 18 | 18 | 18 | 18 | 18 | 18 |
| 3G | | | | | | | |
| Bis-GMA | 35 | 35 | 35 | 35 | 35 | 35 | 35 |
| UDMA | | | | | | | |
| MDP | | | | | | | |
| CQ | 1.8 | 1.8 | 1.8 | 1.8 | 1.8 | 1.8 | 1.8 |
| TPO | 1.2 | 1.2 | 1.2 | 1.2 | 1.2 | 1.2 | 1.2 |
| EPA | 3.5 | 3.5 | 3.5 | 3.5 | 3.5 | 3.5 | 3.5 |
| BPO | | | | | | | |
| PA | | | | | | | |
| BHT | 0.5 | 0.5 | 0.5 | 0.5 | 0.5 | 0.5 | 0.5 |
| INORGANIC FILLER | 2 | 2 | 2 | 2 | 2 | 2 | 2 |
| TOTAL | 100 | 100 | 100 | 100 | 100 | 100 | 100 |
| TOOTH SUBSTANCE DECALCIFICATION INHIBITING EFFECT | | | | | | | |
| MINERAL LOSS [VOLUME %-μm] | 3042 | 2979 | 3211 | 2742 | 2955 | 2719 | 2974 |
| EVALUATION | A | A | B | A | A | A | A |

TABLE 1B-continued

| | EXAMPLE | | | | | | |
|---|---|---|---|---|---|---|---|
| | 8 | 9 | 10 | 11 | 12 | 13 | 14 |
| ADHESIVENESS | | | | | | | |
| ENAMEL | A | A | A | A | A | A | A |
| DENTIN | A | A | A | A | A | A | A |

TABLE 2

| | COMPARATIVE EXAMPLE | | | | | | |
|---|---|---|---|---|---|---|---|
| | 1 | 2 | 3 | 4 | 5 | 6 | 7 |
| GLASS POWDER | | | | | | | |
| Zn | | | | | 4.6 | | |
| F | | 13.5 | 13.1 | 12.0 | 11.2 | 9.4 | 13.2 |
| Al | | 25.9 | 23.9 | 25.9 | 21.3 | 21.4 | 25.5 |
| Si | | 23.8 | 24.0 | 25.1 | 23.6 | 20.9 | 23.3 |
| Ca | | | 0.3 | 0.1 | 1.8 | | |
| P | | 1.3 | 4.6 | 3.5 | 3.5 | 1.0 | 4.4 |
| Sr | | 35.5 | 34.1 | 31.9 | 28.0 | 47.3 | 21.5 |
| La | | | | | | 6.0 | 4.6 |
| Na | | | | 1.5 | | | 3.2 |
| K | | | | | | | 4.3 |
| TOTAL | | 100 | 100 | 100 | 100 | 100 | 100 |
| NUMBER AVERAGE PARTICLE DIAMETER [μ m] | | 0.7 | 0.6 | 0.6 | 0.6 | 0.7 | 0.4 |
| ADHESIVE | | | | | | | |
| GLASS POWDER | | 20 | 20 | 20 | 20 | 20 | 20 |
| HEMA | 21 | 18 | 18 | 18 | 18 | 18 | 18 |
| NPG | | | | | | | |
| 3G | 21 | 18 | 18 | 18 | 18 | 18 | 18 |
| Bis-GMA | 40 | 35 | 35 | 35 | 35 | 35 | 35 |
| UDMA | | | | | | | |
| CQ | 2 | 1.8 | 1.8 | 1.8 | 1.8 | 1.8 | 1.8 |
| TPO | 1.5 | 1.2 | 1.2 | 1.2 | 1.2 | 1.2 | 1.2 |
| EPA | 4 | 3.5 | 3.5 | 3.5 | 3.5 | 3.5 | 3.5 |
| BPO | | | | | | | |
| PA | | | | | | | |
| BHT | 0.5 | 0.5 | 0.5 | 0.5 | 0.5 | 0.5 | 0.5 |
| INORGANIC FILLER | 10 | 2 | 2 | 2 | 2 | 2 | 2 |
| TOTAL | 100 | 100 | 100 | 100 | 100 | 100 | 100 |
| TOOTH SUBSTANCE DECALCIFICATION INHIBITING EFFECT | | | | | | | |
| MINERAL LOSS [VOLUME %-μ m] | 4542 | 3615 | 3890 | 3865 | 4050 | 3892 | 3769 |
| EVALUATION | C | C | C | C | C | C | C |
| ADHESIVENESS | | | | | | | |
| ENAMEL | A | A | A | A | A | A | A |
| DENTIN | A | A | A | A | A | A | A |

As can be appreciated from Table 1A, Table 1B and Table 2, the adhesives of Examples 1 to 14 have high tooth substance decalcification inhibiting effects and high adhesiveness.

In contrast, because the adhesive of Comparative Example 1 does not contain glass powder, the tooth substance decalcification inhibiting effect is comparatively low.

Also, in the adhesives of Comparative Examples 2 to 7, the content of aluminum in the glass powder used was in the range from 21.3 to 25.9 mass % in terms of the amount of aluminum oxide ($Al_2O_3$) in the glass powder, and as a result, the tooth substance decalcification inhibiting effects of these adhesives are comparatively low.

The present application is based on and claims priority to Japanese Patent Application No. 2016-117348 filed on Jun. 13, 2016, the entire contents of which are herein incorporated by reference.

The invention claimed is:

1. A dental polymerizable composition comprising:
   a glass powder and a (meth)acrylate;
   wherein the glass powder includes zinc, silicon, and fluorine and is, substantially free of aluminum, and
   wherein zinc content, in terms of an amount of zinc oxide, ZnO, in the glass powder is in a range from 10 to 60 mass %; silicon content, in terms of an amount of silicon oxide, $SiO_2$ in the glass powder is in a range from 15 to 50 mass %; and fluorine content of the glass powder is in a range from 1 to 30 mass %.

2. The dental polymerizable composition according to claim 1, wherein the zinc content, in terms of the amount of zinc oxide, ZnO, in the glass powder is in a range from 20 to 60%.

3. The dental polymerizable composition according to claim 1, further comprising:
   at least one of calcium and lanthanum.

4. The dental polymerizable composition according to claim 1, wherein the fluorine content of the glass powder is in a range from 1 to 6.8%.

5. The dental polymerizable composition according to claim 1, further comprising:
   strontium,
   wherein strontium content, in terms of an amount of strontium oxide, SrO, in the glass powder is in a range from 0 to 12.4 mass %.

* * * * *